United States Patent [19]

Van der Veer et al.

[11] Patent Number: 5,291,136
[45] Date of Patent: Mar. 1, 1994

[54] VARIABLE ANGLE EDDY CURRENT PROBE

[75] Inventors: William R. Van der Veer; Glenn M. Light, both of San Antonio, Tex.

[73] Assignee: Systems Research Laboratories, Inc., Dayton, Ohio

[21] Appl. No.: 31,013

[22] Filed: Mar. 11, 1993

Related U.S. Application Data

[63] Continuation of Ser. No. 803,746, Dec. 4, 1991, abandoned, which is a continuation of Ser. No. 570,895, Aug. 22, 1990, abandoned.

[51] Int. Cl.$^5$ .................. G01R 33/12; G01N 27/82
[52] U.S. Cl. .................................... 324/262; 324/238
[58] Field of Search ............... 324/219, 220, 234, 238, 324/262; 901/15, 44

[56] References Cited

U.S. PATENT DOCUMENTS

| | | | |
|---|---|---|---|
| 4,123,708 | 10/1978 | Vild et al. | 324/225 |
| 4,139,822 | 2/1979 | Urich et al. | 324/219 |
| 4,600,355 | 7/1985 | Johnson | 901/15 |

Primary Examiner—Walter E. Snow
Attorney, Agent, or Firm—Biebel & French

[57] ABSTRACT

An eddy current probe for nondestructive testing, having a rotatable shoe that holds the eddy current coil. The probe is attached to an arm of automated eddy current test equipment, and has a coil-containing shoe that may be rotated to a desired angle with respect to the surface to be inspected. The probe has a motor and pulley system for providing this rotational motion.

13 Claims, 3 Drawing Sheets

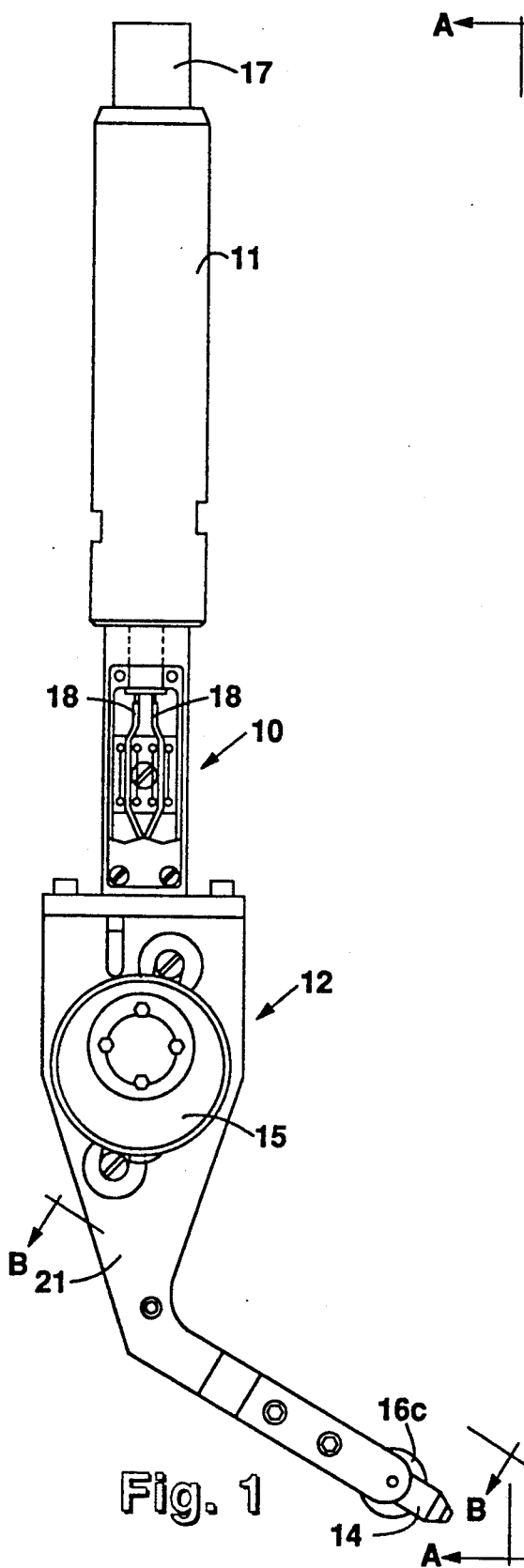
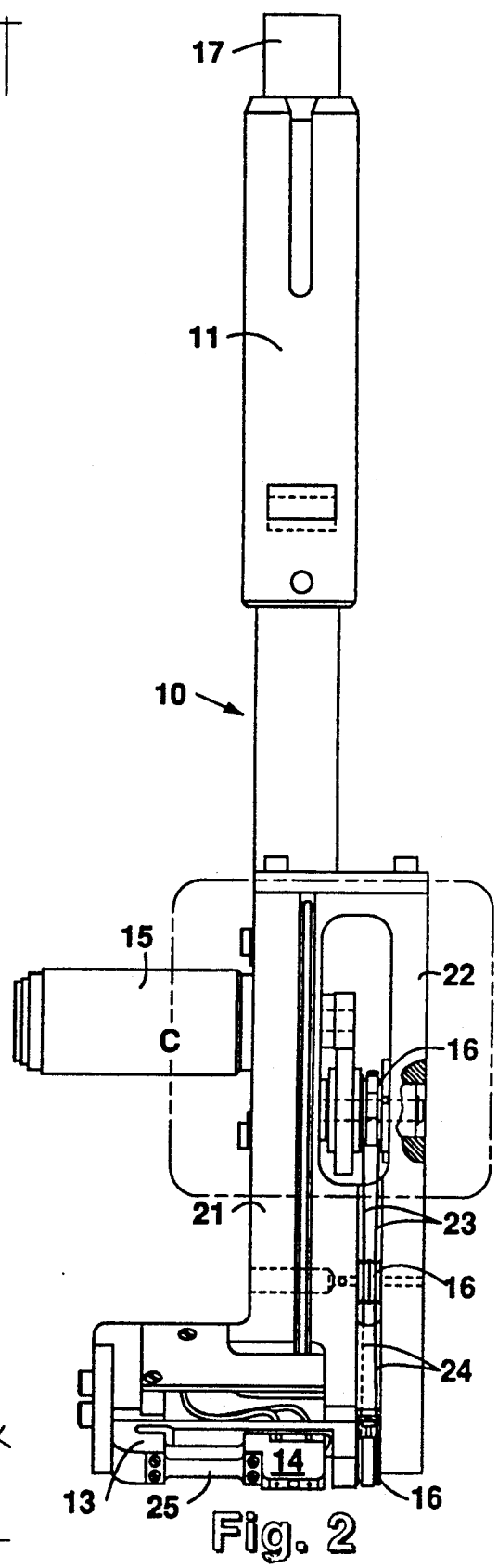

VARIABLE ANGLE EDDY CURRENT PROBE

This application is a continuation of application Ser. No. 07/803,746 filed Dec. 4, 1991, now abandoned, which is a continuation of application Ser. No. 07/570,895 filed Aug. 22, 1990, now abandoned.

TECHNICAL FIELD OF THE INVENTION

This invention relates to nondestructive testing, and more particularly to an eddy current probe having a motorized coil-containing shoe that permits a variable inspection angle.

BACKGROUND OF THE INVENTION

Eddy current testing is one method of nondestructive testing that uses electromagnetic wave phenomena. Like all such methods, the testing is indirect: the material properties to be measured must be correlated with appropriate electromagnetic properties. This correlation succeeds, provided that the test conditions are well controlled and that the instrumentation is well calibrated.

Eddy current testing involves the observation of the interaction between electromagnetic fields and metals. The basic requirements are a coil or coils carrying an alternating current, to which an electrically conductive specimen is subjected, and a means of measuring the response current or voltage. The alternating current through the coil, of a chosen frequency, produces eddy currents in the specimen, which in turn produce fields in the coil.

One means of applying the current to the specimen is holding the test coil in a probe that is moved over the surface of the specimen. A part of this test process is maintaining the correct angle between the specimen and the coil. Ideally, this relationship is a constant, and analysis is easiest if the coil is kept perpendicular to the surface of the specimen. For flat surfaces, this goal is easily met, but for surfaces having irregular shapes, the probe must be adjusted according to surface variations. For example, many applications involve testing parts of equipment that may have irregular surface features, such as curves, bolt holes, flanges and the like.

In application, the basic method of testing involves moving the probe over the specimen surface. Sophisticated automated systems have been developed for providing the exciting current, moving the probe, and analyzing the response signal.

To maintain a constant angle between the coil and the test surface, existing test systems use a set of probes designed to access all possible surfaces. For example, one probe might be designed for flat surfaces, whereas another probe might be designed for reaching into a bolt hole or around a corner of a flange. As the test arm is moved over the specimen, appropriate probes are installed. Mechanical manipulators can be used to vary the angle to some extent, but the range of manipulation is limited, and inadequate for some test geometries.

A problem with using multiple probes is that each probe must be recalibrated once installed. This is due to the fact that each eddy current coil is somewhat different in electromagnetic properties. This recalibration results in substantial overhead in terms of time during the test process. In some irregular test surface geometries, the total inspection time may be dominated by the calibration time, rather than the actual test time. Thus, a need exists for a method of eddy current testing that eliminates the need for multiple probes.

SUMMARY OF THE INVENTION

One aspect of the invention is an eddy current probe having an shoe, which holds an eddy current coil and which may be rotated so that the probe can be kept normal to the surface under inspection over a large range of angles. The probe comprises a connector assembly for attaching it to a mechanical arm of an eddy current test system, and for providing connections for electrical signals. A body is attached to the connector assembly and has an outer fork and an inner fork, each having an angled upper leg and a lower leg that are spaced apart at their lowermost ends. A shoe support frame is rotatably attached between the lowermost ends of the lower legs. A shoe is attached to the shoe support frame and holds an eddy current coil. A motor attached to an upper leg of one fork provides rotational motion, and a pulley system imposed between the forks translates this rotational motion to the shoe support frame.

A technical advantage of the invention is that eddy current testing can be performed much more quickly. There is no need to change probes for different surfaces. The invention is especially useful with automated test equipment, which can be programmed to move a mechanical arm and rotate the probe shoe so that a single probe can be used for an entire test pattern.

BRIEF DESCRIPTION OF THE DRAWINGS

FIG. 1 is a side view of the eddy current probe in accordance with the invention.

FIG. 2 shows the eddy current probe of FIG. 1 from viewpoint A.

DETAILED DESCRIPTION OF THE INVENTION

Figure 3:
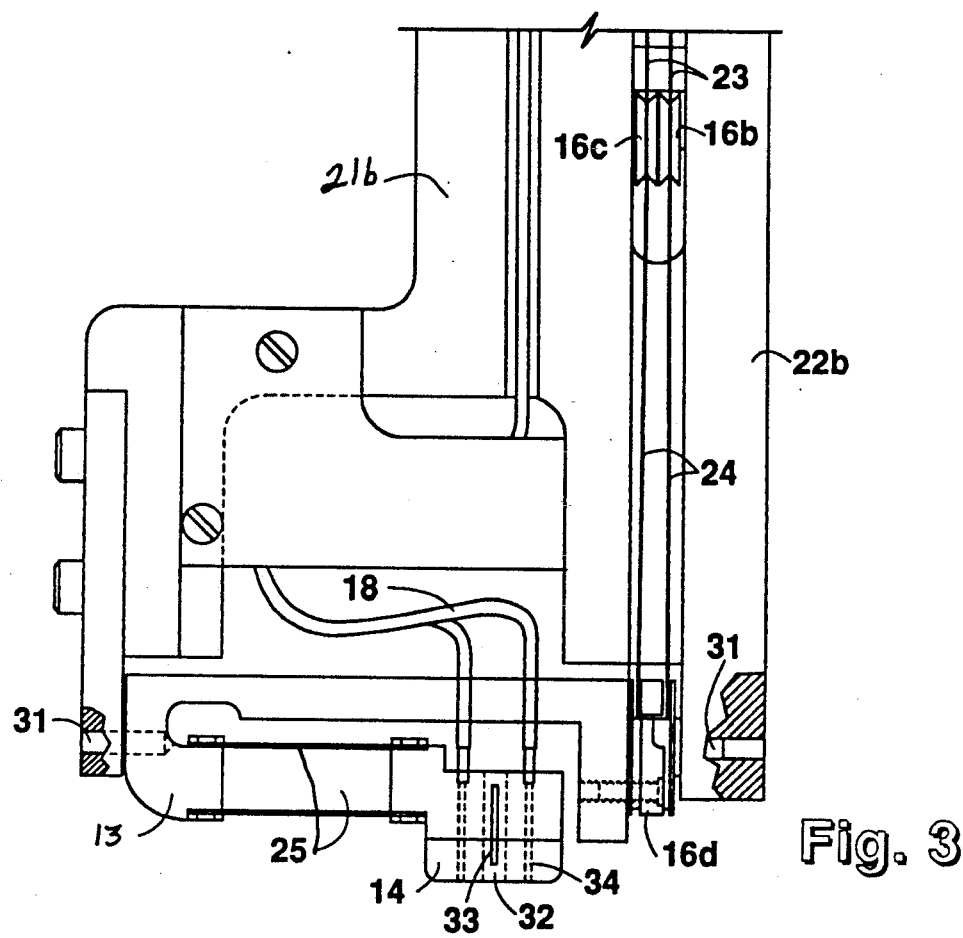
FIG. 3 shows the eddy current probe of FIG. 1 along line B—B, rotated 30 degrees counterclockwise.

FIG. 1 is a side view of eddy current probe 10. FIG. 2 is a front view of probe 10 along line A—A of FIG. 1, and FIG. 3 illustrates probe 10 from viewpoint B of FIG. 1, rotated 30 degrees counterclockwise. The main components of probe 10 are connector assembly 11, body 12, a shoe support frame 13, a shoe 14, a motor 15, and pulley system 16.

In operation, probe 10 is typically used with an automated eddy current test system, having signal generators, a detector, an analyzer, and a mechanical means of moving an arm, to which probe 10 is attached. This instrumentation and the operation of eddy current probe 10 are described below in connection with FIG. 5.

Connector assembly 11 is a means for attaching probe 10 to the arm of the rest of the eddy current test system. Connector assembly 11 provides signal and power lines from the eddy current power source and other instrumentation. In the preferred embodiment, connector 11 uses a multiple pin connector, for example, the round 10-pin connector 17 of FIG. 1, to connect these lines. Air tubes 18 carry air for cooling the eddy current coil, as explained below.

Figure 4:
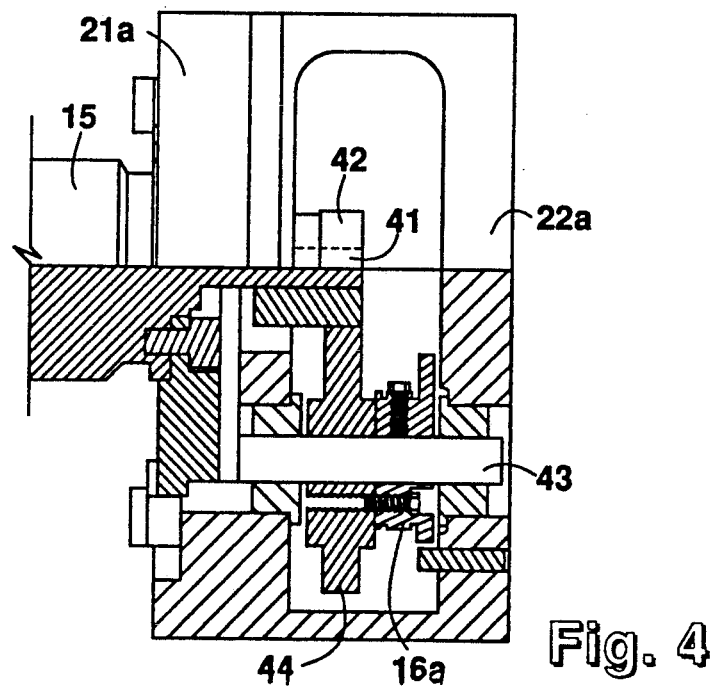
FIG. 4 provides further detail of area C of FIG. 2.

Body 12 is comprised of an outer fork 21 and an inner fork 22, as shown in FIGS. 2-4. Each fork 21 and 22 is angled, so that each has an upper leg 21a and 22a and a lower leg 21b and 22b. The angle between upper leg 21a and 21b of outer fork 21 is about 120 degrees plus or minus 60 degrees, and ideally is about 120 degrees. The angle between upper leg 22a and lower leg 22b of inner fork 22 is approximately the same. As explained below in connection with FIG. 5, this angle provides the greatest range of access for a large number of surface configurations. Outer fork 21 and inner fork 22 are spaced apart, and as explained below, this permits inspection shoe support frame 13 and pulley system 16 to be interposed between them.

FIGS. 2 and 3 illustrate lower legs 21b and 22b of outer fork 21 and inner fork 22 in further detail, as well as the manner in which inspection shoe support frame 13 is interposed between them at their lowermost ends. Shoe support frame 13 is suspended between the inside of lower leg 21b of outer fork 21 and the inside of lower leg 22b of inner fork 22 by means of pivot pins 31, which permit shoe support frame 13 to rotate.

Shoe support frame 13 includes two springs 25, which are placed between shoe 14 and one of the rotating ends of shoe support frame 13. Springs 25 provide up and down compliance of shoe 14 with respect to the surface under test, which ensures that lift-off of shoe 14 remains within an acceptable tolerance range. In the embodiment of this description, springs 25 are two thin strips of flexible material, spaced near a front end and a back end of shoe 14. To accommodate springs 25, the space between lower legs 21b and 22b may be widened.

Shoe 14 is attached to shoe support frame 13, preferably via spring 25. Ideally, shoe 14 has a ceramic filled epoxy tip, which resists wear due to friction between the surface under inspection and the surface of shoe 14.

As shown in FIG. 3, shoe 14 includes a compartment 32 for inserting an eddy current coil 33. In the embodiment described herein, coil 33 is a double-ended reflection differential coil, but depending on inspection requirements, other types may be used. The present invention is especially useful with a very small coil 33. For example, a coil 33 that is 0.080 inches high and 0.0060 inches in diameter has been successfully used.

Air ducts 34 within shoe 14 provide forced air cooling for coil 33. The air is provided by air tubes 18 from a source.

Referring now to FIG. 4, which is a detailed view of area C of FIG. 2, motor 15 provides rotating motion and, in combination with pulley system 16, provides a means for rotating shoe support frame 13. Typically, motor 15 uses direct current. A stepper motor may be used. Ideally, motor 15 is one of the commercially available micromanipulator motors, made very small so that probe 10 may be small, easily manipulated, and capable of accessing small access regions. As explained below, the motor shaft 41 of motor 15 may be used in conjunction with gears 42 and 44 to improve the mechanical effect of motor 15. In the preferred embodiment, motor 15 includes an encoder (not shown) for providing a readout of the shoe rotation angle at a given time.

Pulley system 16 translates the motion produced by motor 15 to inspection shoe 14. In the preferred embodiment, pulley system 16 is comprised of four pulleys: a drive pulley 16a, two middle cable pulleys 16b and 16c, and a lower cable pulley 16d.

Drive pulley 16a is placed on gear shaft 43 between the upper legs 21a and 22a of outer fork 21 and inner fork 22. A pulley gear 44 is also placed on shaft 43, such that it engages the motor gear 42 of motor 15. The motion of motor gear 42 drives pulley gear 44, thereby providing rotational motion for pulley 16a.

Referring again to FIGS. 1-3, middle pulleys 16b and 16c are placed between outer fork 21 and inner fork 22 near their angled portion. Lower pulley 16d is placed between outer fork 21 and inner fork 22 at the lowermost portion of lower legs 21b and 22b. Pulley system 16 uses a system of cables, which in the four-pulley embodiment described herein, includes upper cables 23 between drive pulley 16a and middle pulleys 16b and 16c, and lower cables 24 between middle pulleys 16b and 16c and lower pulley 16d.

Figure 5:
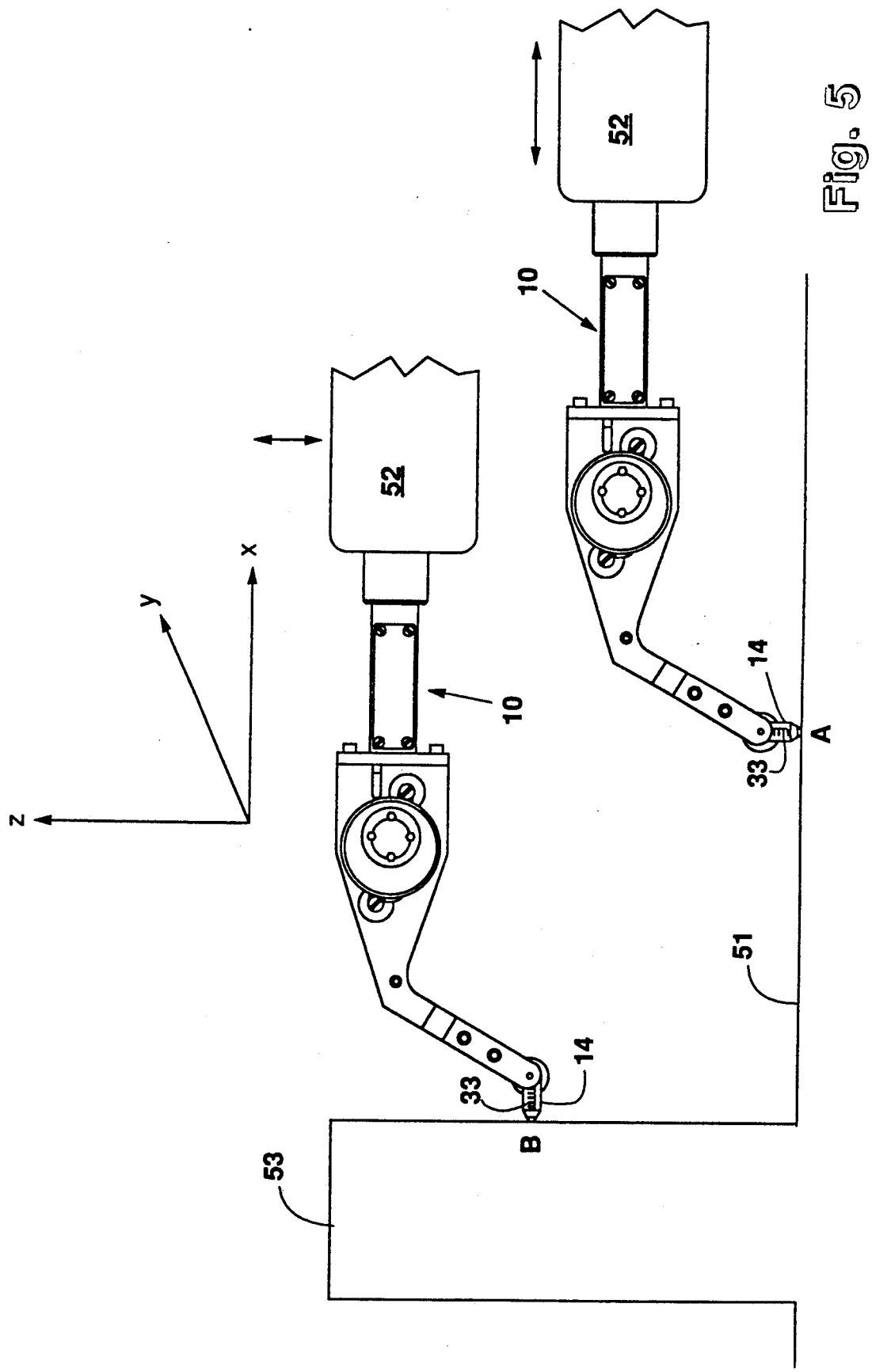
FIG. 5 illustrates the relative motions of the arm of an eddy current test machine and the coil-containing shoe of the probe of FIG. 1 in relation to a surface under test.

FIG. 5 comprises two side views of probe 10, which illustrate the relative motions of the test equipment arm, labeled 52, and inspection shoe 14. Surface 51 represents the surface of an object under test, for example, a part of an airplane engine. As indicated by the example of FIG. 5, surface 51 is irregular and has a known geometry, for example, the right angle of flange 53.

To cover the area of surface 51, arm 52 moves in at least three directions in an x, y, and z plane. In position A, the arm 52 moves in the x, y plane and shoe 14 is rotated at a first angle, so that coil 33 is normal to the surface. In position B, arm 52 moves in the y, z plane, and shoe 14 is rotated at a second angle, 90 degrees from the angle of position A, so that coil 33 continues to be normal to surface 51. In both positions, springs 25 ensure proper lift off.

For a known geometry of the surface of an object to be tested, the combination of motions of arm 52 and shoe 14 can be used to test the entire object without need to change probes. Arm 52 provides gross x, y, z movements and keeps shoe 14 close to the surface. Shoe 14 is rotated to ensure that coil 33 remains at a known angle to the surface, typically normal to the surface. The eddy current test equipment can be programmed so that arm 52 follows a predetermined path, with predetermined rotations of shoe 14.

Although the invention has been described with reference to specific embodiments, this description is not meant to be construed in a limiting sense. Various modifications of the disclosed embodiments, as well as alternative embodiments will be apparent to persons skilled in the art. It is, therefore, contemplated that the appended claims will cover all modifications that fall within the true scope of the invention.

What is claimed is:

1. A probe for use with eddy current test equipment, comprising:

a connector assembly for attaching said probe to an arm of said eddy current test equipment;

a body attached to said connector assembly, said body having an outer fork and an inner fork, wherein said both said outer fork and said inner fork have an upper leg and a lower leg, and wherein said lower legs are spaced apart at their lowermost ends;

a shoe support frame rotatably attached between the lowermost ends of said lower legs;

an eddy current coil;

a shoe for holding said eddy current coil, said shoe having a front surface for engaging a surface to be tested, and a rear surface;

a pair of spaced apart, thin flexible springs attached between said shoe and said shoe support frame for maintaining said front surface of said shoe parallel to the surface to be tested;

a motor attached to said body, said motor providing rotational motion to a motor shaft;

a pulley system imposed between said outer fork and said inner fork, for translating said rotational motion to said shoe support frame, for modifying the position of said eddy current coil; and an encoder carried by said body for sensing the position of said eddy current coil.

2. The probe of claim 1, and further comprising a gear assembly attached to a shaft of said motor for translating said rotational motion of said motor to rotational motion of said drive system.

3. The probe of claim 1, wherein said shoe has a ceramic filled epoxy tip.

4. The probe of claim 1 wherein said shoe has air tubes for providing forced air cooling, said tubes extending from said rear surface of said shoe to openings formed in said front surface.

5. The probe of claim 1, wherein said motor is a micro-manipulator motor.

6. The probe of claim 1, wherein said pulley system comprises a drive pulley between said upper legs of said inner and outer forks and a lower cable pulley between said lower legs of said outer and inner forks.

7. The probe of claim 1, wherein said upper legs and said lower legs of said outer fork and said inner fork are at an angle with respect to each other that is generally the same for said outer fork and said inner fork.

8. The probe of claim 7, wherein said pulley system comprises a drive pulley between said upper legs of said inner and outer forks, a middle cable pulley between the angle portion of said outer and inner forks, and a lower cable pulley between said lower legs of said outer and inner forks.

9. A method of nondestructive materials testing, using eddy current response signals, comprising the steps of:

moving a mechanical arm of eddy current test equipment to a desired position above a test surface;

placing an eddy current coil inside a shoe having a front surface;

supporting the shoe on the arm by means of a pair of spaced apart thin flexible springs oriented to maintain the front surface of the shoe in positive contact with and parallel to the surface being tested;

rotatably attaching the shoe to said arm;

adjusting the angle of said shoe so that the shoe is placed with its front surface parallel and in contact with said surface during testing, using a motor and pulleys attached to said probe; and monitoring the angle of the shoe remotely by means of an encoder.

10. The method of claim 9, and further comprising the step of providing a predetermined pattern of electrical signals to said motor to direct the degree of said rotation.

11. The method of claim 9, and further comprising the step of using a spring to maintain a lift off tolerance of said shoe with respect to said surface.

12. The method of claim 9, and further comprising the step of cooling said eddy current coil with air conducted through air ducts in said shoe.

13. The method of claim 9, and further comprising the step of maintaining said angle such that said coil is constantly normal to said surface.

* * * * *